(12) United States Patent
Eberle et al.

(10) Patent No.: US 9,078,561 B2
(45) Date of Patent: *Jul. 14, 2015

(54) OPTICAL ULTRASOUND RECEIVER

(71) Applicant: Vascular Imaging Corporation, Rancho Cordova, CA (US)

(72) Inventors: Michael J. Eberle, Fair Oaks, CA (US); Diana Margaret Tasker, Fair Oaks, CA (US); Howard Neil Rourke, Sacramento, CA (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,421

(22) Filed: Oct. 14, 2013

(65) Prior Publication Data

US 2014/0142414 A1     May 22, 2014

Related U.S. Application Data

(63) Continuation of application No. 12/571,724, filed on Oct. 1, 2009, now Pat. No. 8,560,048.

(60) Provisional application No. 61/102,216, filed on Oct. 2, 2008.

(51) Int. Cl.
*A61B 5/05*     (2006.01)
*A61B 5/00*     (2006.01)
(Continued)

(52) U.S. Cl.
CPC ........... *A61B 5/0095* (2013.01); *A61B 1/00082* (2013.01); *A61B 1/07* (2013.01);
(Continued)

(58) Field of Classification Search
USPC .......... 600/407, 437, 459, 472, 473, 476, 477
See application file for complete search history.

(56) References Cited

U.S. PATENT DOCUMENTS 3,995,623 A    12/1976   Blake et al.
4,068,191 A    1/1978   Zemon et al.
(Continued)

FOREIGN PATENT DOCUMENTS

CA    2472877 A1    7/2003
DE    2363984 A1    6/1975
(Continued)

OTHER PUBLICATIONS

Surowiec et al., "A Novel Miniature Optical Fibre Probe for MHz Frequency Ultrasound." 1996, IEEE Ultrasonics Symposium, pp. 1051-1054.*

(Continued)

*Primary Examiner* — James Kish
(74) *Attorney, Agent, or Firm* — Schwegman Lundberg & Woessner, P.A.

(57) ABSTRACT

An imaging guidewire can include one or more optical fibers communicating light along the guidewire. At or near its distal end, one or more blazed or other Fiber Bragg Gratings (FBGs) can direct light to a photoacoustic transducer material that provides ultrasonic imaging energy. Returned ultrasound can be sensed by an FBG sensor. A responsive signal can be optically communicated to the proximal end of the guidewire, and processed such as to develop a 2D or 3D image. In an example, the guidewire outer diameter can be small enough such that an intravascular catheter can be passed over the guidewire. To minimize the size of the guidewire, an ultrasound-to-acoustic transducer that is relatively insensitive to the polarization of the optical sensing signal can be used. The ultrasound-to-optical transducer can be manufactured so that it is relatively insensitive to the polarization of the optical sensing signal.

19 Claims, 5 Drawing Sheets

(51) Int. Cl.
  *A61B 8/12* (2006.01)
  *G01H 9/00* (2006.01)
  *A61B 1/00* (2006.01)
  *A61B 1/07* (2006.01)
  *A61B 8/00* (2006.01)

(52) U.S. Cl.
  CPC ............ *A61B 5/0097* (2013.01); *A61B 5/6851* (2013.01); *A61B 8/12* (2013.01); *A61B 8/4483* (2013.01); *G01H 9/004* (2013.01); *Y10T 29/49005* (2013.01)

(56) References Cited

U.S. PATENT DOCUMENTS

| | | |
|---|---|---|
| 4,076,379 A | 2/1978 | Chouinard |
| 4,115,753 A | 9/1978 | Shajenko |
| 4,327,738 A | 5/1982 | Green et al. |
| 4,473,065 A | 9/1984 | Bates |
| 4,522,193 A | 6/1985 | Bates |
| 4,587,972 A | 5/1986 | Morantte, Jr. |
| 4,887,605 A | 12/1989 | Angelsen et al. |
| 4,900,921 A | 2/1990 | Spillman, Jr. |
| 4,917,097 A | 4/1990 | Proudian et al. |
| 4,946,238 A | 8/1990 | Sashin et al. |
| 5,007,705 A | 4/1991 | Morey et al. |
| 5,070,882 A | 12/1991 | Bui et al. |
| 5,095,911 A | 3/1992 | Pomeranz |
| 5,099,090 A | 3/1992 | Allan et al. |
| 5,109,463 A | 4/1992 | Lee |
| 5,135,295 A | 8/1992 | Jen et al. |
| 5,135,486 A | 8/1992 | Eberle et al. |
| 5,156,772 A | 10/1992 | Allan |
| 5,167,233 A | 12/1992 | Eberle et al. |
| 5,183,048 A | 2/1993 | Eberle |
| 5,186,177 A | 2/1993 | O'Donnell et al. |
| 5,226,847 A | 7/1993 | Thomas, III et al. |
| 5,240,004 A | 8/1993 | Walinsky et al. |
| 5,254,112 A | 10/1993 | Sinofsky et al. |
| 5,290,275 A | 3/1994 | Kittrell et al. |
| 5,305,758 A | 4/1994 | Dietz et al. |
| 5,325,860 A | 7/1994 | Seward et al. |
| 5,353,262 A | 10/1994 | Yakymyshyn et al. |
| 5,368,037 A | 11/1994 | Eberle et al. |
| 5,383,467 A | 1/1995 | Auer et al. |
| 5,400,788 A | 3/1995 | Dias et al. |
| 5,427,107 A | 6/1995 | Milo et al. |
| 5,439,000 A | 8/1995 | Gunderson et al. |
| 5,453,575 A | 9/1995 | O'Donnell et al. |
| 5,486,170 A | 1/1996 | Winston et al. |
| 5,558,669 A | 9/1996 | Reynard |
| 5,558,699 A | 9/1996 | Nakashima et al. |
| 5,582,171 A | 12/1996 | Chornenky et al. |
| 5,601,087 A | 2/1997 | Gunderson et al. |
| 5,603,327 A | 2/1997 | Eberle et al. |
| 5,615,675 A | 4/1997 | O'Donnell et al. |
| 5,660,180 A | 8/1997 | Malinowski et al. |
| 5,675,674 A | 10/1997 | Weis |
| 5,680,489 A | 10/1997 | Kersey |
| 5,682,897 A | 11/1997 | Pomeranz |
| 5,684,297 A | 11/1997 | Tardy et al. |
| 5,704,361 A | 1/1998 | Seward et al. |
| 5,718,226 A | 2/1998 | Riza |
| 5,732,046 A | 3/1998 | O'Donnell et al. |
| 5,748,564 A | 5/1998 | Pattanayak |
| 5,779,643 A | 7/1998 | Lum et al. |
| 5,779,644 A | 7/1998 | Eberle et al. |
| 5,830,145 A | 11/1998 | Tenhoff |
| 5,852,233 A | 12/1998 | Arnold et al. |
| 5,857,974 A | 1/1999 | Eberle et al. |
| 5,865,178 A | 2/1999 | Yock |
| 5,872,879 A | 2/1999 | Hamm |
| 5,873,835 A | 2/1999 | Hastings et al. |
| 5,876,344 A | 3/1999 | Baker et al. |
| 5,894,531 A | 4/1999 | Alcoz |
| 5,921,931 A | 7/1999 | O'Donnell et al. |
| 5,938,609 A | 8/1999 | Pomeranz |
| 5,938,615 A | 8/1999 | Eberle et al. |
| 5,944,687 A | 8/1999 | Benett et al. |
| 5,953,477 A | 9/1999 | Wach et al. |
| 5,980,117 A | 11/1999 | Feuer et al. |
| 6,039,701 A | 3/2000 | Sliwa et al. |
| 6,049,958 A | 4/2000 | Eberle et al. |
| 6,057,927 A | 5/2000 | Levesque et al. |
| 6,078,831 A | 6/2000 | Belef et al. |
| 6,080,109 A | 6/2000 | Baker et al. |
| 6,100,969 A | 8/2000 | Perez |
| 6,111,645 A | 8/2000 | Tearney et al. |
| 6,123,673 A | 9/2000 | Eberle et al. |
| 6,134,003 A | 10/2000 | Tearney et al. |
| 6,210,339 B1 | 4/2001 | Kiepen et al. |
| 6,222,970 B1 | 4/2001 | Wach et al. |
| 6,228,078 B1 | 5/2001 | Eggers et al. |
| 6,238,347 B1 | 5/2001 | Nix et al. |
| 6,248,076 B1 | 6/2001 | White et al. |
| 6,261,246 B1 | 7/2001 | Pantages et al. |
| 6,282,011 B1 | 8/2001 | Tearney et al. |
| 6,283,920 B1 | 9/2001 | Eberle et al. |
| 6,292,610 B1 | 9/2001 | O'Rourke et al. |
| 6,306,096 B1 | 10/2001 | Seward et al. |
| 6,315,732 B1 | 11/2001 | Suorsa et al. |
| 6,330,383 B1 | 12/2001 | Cai et al. |
| 6,379,325 B1 | 4/2002 | Benett et al. |
| 6,416,234 B1 | 7/2002 | Wach et al. |
| 6,421,164 B2 | 7/2002 | Tearney et al. |
| 6,494,836 B2 | 12/2002 | Ogawa |
| 6,538,807 B2 | 3/2003 | Kakui et al. |
| 6,575,965 B1 | 6/2003 | Fitch et al. |
| 6,585,660 B2 | 7/2003 | Dorando et al. |
| 6,611,633 B1 | 8/2003 | Vohra et al. |
| 6,618,916 B1 | 9/2003 | Eberle et al. |
| 6,659,957 B1 | 12/2003 | Vardi et al. |
| 6,779,257 B2 | 8/2004 | Kiepen et al. |
| 6,783,494 B2 | 8/2004 | Ogawa |
| 6,907,163 B2 | 6/2005 | Lewis |
| 6,938,474 B2 | 9/2005 | Melvås |
| 6,948,859 B2 | 9/2005 | Anderson |
| 7,082,238 B2 | 7/2006 | Nishimura |
| 7,097,620 B2 | 8/2006 | Corl et al. |
| 7,184,148 B2 | 2/2007 | Alphonse |
| 7,190,464 B2 | 3/2007 | Alphonse |
| 7,242,480 B2 | 7/2007 | Alphonse |
| 7,242,832 B2 | 7/2007 | Carlin et al. |
| 7,245,789 B2 | 7/2007 | Bates et al. |
| 7,417,740 B2 | 8/2008 | Alphonse et al. |
| 7,447,388 B2 | 11/2008 | Bates et al. |
| 7,527,594 B2 | 5/2009 | Vardi et al. |
| 7,599,588 B2 | 10/2009 | Eberle et al. |
| 7,660,492 B2 | 2/2010 | Bates et al. |
| 7,753,852 B2 | 7/2010 | Maschke |
| 7,881,573 B2 | 2/2011 | Eberle et al. |
| 8,059,923 B2 | 11/2011 | Bates et al. |
| 8,218,927 B2 | 7/2012 | Chang et al. |
| 8,320,723 B2 | 11/2012 | Eberle et al. |
| 8,391,652 B2 | 3/2013 | Bates et al. |
| 8,560,048 B2 | 10/2013 | Eberle et al. |
| 8,731,340 B2 | 5/2014 | Bates et al. |
| 8,926,519 B2 | 1/2015 | Vardi et al. |
| 2001/0021843 A1 | 9/2001 | Bosselmann et al. |
| 2001/0046352 A1 | 11/2001 | Ohta et al. |
| 2002/0039463 A1 | 4/2002 | Degertekin et al. |
| 2002/0041735 A1 | 4/2002 | Cai et al. |
| 2002/0059827 A1 | 5/2002 | Smith |
| 2003/0026546 A1 | 2/2003 | Deliwala |
| 2003/0181802 A1* | 9/2003 | Ogawa ......................... 600/407 |
| 2003/0187369 A1 | 10/2003 | Lewis et al. |
| 2004/0067000 A1 | 4/2004 | Bates et al. |
| 2004/0116800 A1 | 6/2004 | Helfer et al. |
| 2004/0182315 A1 | 9/2004 | Laflamme, Jr. et al. |
| 2005/0121734 A1 | 6/2005 | Degertekin et al. |
| 2005/0131289 A1 | 6/2005 | Aharoni et al. |
| 2005/0238292 A1 | 10/2005 | Barnes et al. |
| 2006/0067616 A1 | 3/2006 | Kanji et al. |
| 2007/0116408 A1 | 5/2007 | Eberle et al. |

(56) References Cited

U.S. PATENT DOCUMENTS

| | | | |
|---|---|---|---|
| 2007/0133925 | A1 | 6/2007 | Bates et al. |
| 2008/0077225 | A1 | 3/2008 | Carlin et al. |
| 2008/0114254 | A1 | 5/2008 | Matcovitch et al. |
| 2008/0119739 | A1 | 5/2008 | Vardi et al. |
| 2009/0059727 | A1 | 3/2009 | Bates et al. |
| 2010/0014810 | A1 | 1/2010 | Eberle et al. |
| 2010/0087732 | A1 | 4/2010 | Eberle et al. |
| 2010/0135111 | A1 | 6/2010 | Bates et al. |
| 2011/0123154 | A1 | 5/2011 | Eberle et al. |
| 2012/0108943 | A1 | 5/2012 | Bates et al. |
| 2013/0148933 | A1 | 6/2013 | Eberle et al. |
| 2013/0178729 | A1 | 7/2013 | Bates et al. |
| 2014/2549751 | | 9/2014 | Bates et al. |

FOREIGN PATENT DOCUMENTS

| | | | |
|---|---|---|---|
| EP | 0478410 | A1 | 4/1992 |
| EP | 1059878 | A1 | 12/2000 |
| EP | 1152240 | A2 | 11/2001 |
| GB | 2270159 | A | 3/1994 |
| JP | 59158699 | | 9/1984 |
| JP | 63054151 | A | 3/1988 |
| JP | 63102421 | A | 5/1988 |
| JP | 02503279 | T2 | 10/1990 |
| JP | 04355415 | A | 12/1992 |
| JP | 05015536 | A2 | 1/1993 |
| JP | 05034550 | A | 2/1993 |
| JP | 05220152 | | 8/1993 |
| JP | 06003550 | A | 1/1994 |
| JP | 08112289 | A2 | 5/1996 |
| JP | 9010215 | | 1/1997 |
| JP | 09187513 | A | 7/1997 |
| JP | 10073742 | A | 3/1998 |
| JP | 10505920 | T | 6/1998 |
| JP | 10507036 | | 7/1998 |
| JP | 10510364 | | 10/1998 |
| JP | 11194280 | | 7/1999 |
| JP | 11243596 | A | 9/1999 |
| JP | 11514432 | | 12/1999 |
| JP | 2001091785 | A | 4/2001 |
| JP | 2002514455 | A | 5/2002 |
| JP | 2003232964 | A | 8/2003 |
| JP | 2004085756 | A | 3/2004 |
| JP | 2004177549 | A | 6/2004 |
| JP | 2005079177 | A | 3/2005 |
| JP | 4733982 | A | 4/2011 |
| WO | WO-8809150 | A1 | 1/1988 |
| WO | WO-8907419 | A1 | 8/1989 |
| WO | WO-9739691 | A1 | 10/1997 |
| WO | WO-9958059 | A1 | 11/1999 |
| WO | WO-0049938 | A1 | 8/2000 |
| WO | WO-0121244 | A1 | 3/2001 |
| WO | WO-0219898 | A3 | 3/2002 |
| WO | WO-02054948 | A1 | 7/2002 |
| WO | WO-02075404 | A1 | 9/2002 |
| WO | WO-03057061 | | 7/2003 |
| WO | WO-2004008070 | | 1/2004 |
| WO | WO-2004029667 | | 4/2004 |
| WO | WO-2004032746 | A2 | 4/2004 |
| WO | WO-2004077100 | | 9/2004 |
| WO | WO-2004090484 | | 10/2004 |
| WO | WO-2007062050 | A2 | 5/2007 |
| WO | WO-2007062050 | A3 | 5/2007 |
| WO | WO-2010039950 | A1 | 4/2010 |

OTHER PUBLICATIONS

"U.S. Appl. No. 09/623,248, Examiner Interview Summary filed Nov. 6, 2003", 1 pg.

"U.S. Appl. No. 09/623,248, Notice of Allowance mailed Jan. 13, 2003", 7 pgs.

"U.S. Appl. No. 09/623,248, Notice of Allowance mailed Jun. 2, 2003", 7 pgs.

"U.S. Appl. No. 09/623,248, Notice of Allowance mailed Jul. 11, 2003", 8 pgs.

"U.S. Appl. No. 09/623,248, Request for Continued Examination filed Apr. 14, 2003", 6 pgs.

"U.S. Appl. No. 09/623,248, Supplemental Notice of Allowability mailed Oct. 7, 2003", 6 pgs.

"U.S. Appl. No. 10/266,082, Non Final Office Action mailed Oct. 4, 2005", 5 pgs.

"U.S. Appl. No. 10/266,082, Non-Final Office Action mailed Apr. 5, 2006", 7 pgs.

"U.S. Appl. No. 10/266,082, Notice of Allowance mailed Jan. 12, 2005", 5 pgs.

"U.S. Appl. No. 10/266,082, Notice of Allowance mailed Jan. 16, 2007", 5 pgs.

"U.S. Appl. No. 10/266,082, Notice of Allowance mailed Mar. 22, 2007", 5 pgs.

"U.S. Appl. No. 10/266,082, Notice of Allowance mailed Aug. 26, 2004", 8 pgs.

"U.S. Appl. No. 10/266,082, Notice of Allowance mailed Sep. 22, 2006", 4 pgs.

"U.S. Appl. No. 10/266,082, Response filed Jan. 3, 2006 to Non Final Office Action mailed Oct. 4, 2005", 10 pgs.

"U.S. Appl. No. 10/266,082, Response filed Jul. 5, 2006 to Non Final Office Action mailed Apr. 5, 2006", 9 pgs.

"U.S. Appl. No. 10/266,082, Response filed Jul. 28, 2004 to Restriction Requirement Jun. 29, 2004", 2 pgs.

"U.S. Appl. No. 10/266,082, Restriction Requirement mailed Jun. 29, 2004", 5 pgs.

"U.S. Appl. No. 10/685,226, Advisory Action mailed Apr. 17, 2006", 3 pgs.

"U.S. Appl. No. 10/685,226, Final Office Action mailed Jan. 13, 2006", 6 pgs.

"U.S. Appl. No. 10/685,226, Non Final Office Action mailed Jan. 18, 2007", 6 pgs.

"U.S. Appl. No. 10/685,226, Non Final Office Action mailed Jun. 15, 2005", 4 pgs.

"U.S. Appl. No. 10/685,226, Non Final Office Action mailed Jul. 24, 2006", 7 pgs.

"U.S. Appl. No. 10/685,226, Notice of Allowance mailed Oct. 18, 2007", 5 pgs.

"U.S. Appl. No. 10/685,226, Preliminary Amendment filed Oct. 14, 2003", 1 pg.

"U.S. Appl. No. 10/685,226, Response filed Mar. 13, 2006 to Final Office Action mailed Jan. 13, 2006", 12 pgs.

"U.S. Appl. No. 10/685,226, Response filed Apr. 18, 2007 to Non-Final Office Action mailed Jan. 18, 2007", 10 pgs.

"U.S. Appl. No. 10/685,226, Response filed Oct. 14, 2005 to Non Final Office Action mailed Jun. 15, 2005", 15 pgs.

"U.S. Appl. No. 10/685,226, Response filed Oct. 23, 2006 to Non Final Office Action mailed Jul. 24, 2006", 9 pgs.

"U.S. Appl. No. 11/285,499, Advisory Action mailed Jun. 24, 2008", 4 pgs.

"U.S. Appl. No. 11/285,499, Decision on Pre-Appeal Brief Request mailed Sep. 9, 2008", 2 pgs.

"U.S. Appl. No. 11/285,499, Final Office Action mailed Jan. 25, 2008", 7 pgs.

"U.S. Appl. No. 11/285,499, Non Final Office Action mailed May 16, 2007", 13 pgs.

"U.S. Appl. No. 11/285,499, Non-Final Office Action mailed Nov. 13, 2008", 7 pgs.

"U.S. Appl. No. 11/285,499, Notice of Allowance mailed May 27, 2009", 6 pgs.

"U.S. Appl. No. 11/285,499, Pre-Appeal Brief Request filed Jul. 24, 2008", 5 pgs.

"U.S. Appl. No. 11/285,499, Response filed Feb. 15, 2007 to Restriction Requirement mailed Jan. 26, 2007", 12 pgs.

"U.S. Appl. No. 11/285,499, Response filed Apr. 13, 2009 to Non Final Office Action mailed Nov. 13, 2008", 14 pgs.

"U.S. Appl. No. 11/285,499, Response filed May 27, 2008 to Final Office Action mailed Jan. 25, 2008", 9 pgs.

"U.S. Appl. No. 11/285,499, Response filed Oct. 16, 2007 to Non-Final Office Action mailed May 16, 2007", 11 pgs.

"U.S. Appl. No. 11/285,499, Restriction Requirement mailed Jan. 26, 2007", 4 pgs.

(56) References Cited

OTHER PUBLICATIONS

"U.S. Appl. No. 11/674,568, Non-Final Office Action mailed Jan. 7, 2008", 6 pgs.
"U.S. Appl. No. 11/674,568, Notice of Allowance mailed Jun. 25, 2008", 4 pgs.
"U.S. Appl. No. 11/674,568, Response filed Apr. 21, 2008 to Non Final Office Action mailed Jan. 7, 2008", 7 pgs.
"U.S. Appl. No. 11/674,568, Response filed Oct. 16, 2007 to Restriction Requirement mailed Sep. 17, 2007", 7 pgs.
"U.S. Appl. No. 11/674,568, Restriction Requirement mailed Sep. 17, 2007", 6 pgs.
"U.S. Appl. No. 12/020,736, Final Office Action mailed Oct. 12, 2012", 15 pgs.
"U.S. Appl. No. 12/020,736, Final Office Action mailed Oct. 25, 2013", 17 pgs.
"U.S. Appl. No. 12/020,736, Non Final Office Action mailed Jun. 4, 2013", 17 pgs.
"U.S. Appl. No. 12/020,736, Non Final Office Action mailed Sep. 30, 2011", 13 pgs.
"U.S. Appl. No. 12/020,736, Non Final Office Action mailed Dec. 10, 2010", 10 pgs.
"U.S. Appl. No. 12/020,736, Response filed Mar. 30, 2012 to Non Final Office Action mailed Sep. 30, 2011", 17 pgs.
"U.S. Appl. No. 12/020,736, Response filed Jun. 10, 2011 to Non-Final Office Action mailed Dec. 10, 2010", 9 pgs.
"U.S. Appl. No. 12/020,736, Response filed Oct. 4, 2013 to Non Final Office Action mailed Jun. 4, 2013", 18 pgs.
"U.S. Appl. No. 12/020,736, Response filed Dec. 18, 2013 to Final Office Action mailed Oct. 25, 2013", 11 pgs.
"U.S. Appl. No. 12/020,736, Response filed Apr. 12, 2013 to Final Office Action mailed Oct. 12, 2012", 17 pgs.
"U.S. Appl. No. 12/263,978, Notice of Allowance mailed Sep. 22, 2009", 6 pgs.
"U.S. Appl. No. 12/571,724, Examiner Interview Summary mailed May 22, 2013", 3 pgs.
"U.S. Appl. No. 12/571,724, Final Office Action mailed Jan. 4, 2013", 13 pgs.
"U.S. Appl. No. 12/571,724, Non Final Office Action mailed Apr. 18, 2012", 11 pgs.
"U.S. Appl. No. 12/571,724, Notice of Allowance mailed Jun. 11, 2013", 6 pgs.
"U.S. Appl. No. 12/571,724, Response filed Jun. 4, 2013 to Final Office Action mailed Jan. 4, 2013", 13 pgs.
"U.S. Appl. No. 12/571,724, Response filed Oct. 16, 2012 to Non Final Office Action mailed Apr. 18, 2012", 12 pgs.
"U.S. Appl. No. 12/572,511, Non-Final Office Action mailed Jun. 1, 2010", 8 pgs.
"U.S. Appl. No. 12/572,511, Notice of Allowance mailed Sep. 23, 2010", 6 pgs.
"U.S. Appl. No. 12/572,511, Response filed May 17, 2010 to Restriction Requirement mailed May 10, 2010", 7 pgs.
"U.S. Appl. No. 12/572,511, Response filed Sep. 1, 2010 to Non Final Office Action mailed Jun. 1, 2010", 9 pgs.
"U.S. Appl. No. 12/572,511, Restriction Requirement mailed May 10, 2010", 5 pgs.
"U.S. Appl. No. 12/701,228, Notice of Allowance mailed Apr. 22, 2011", 8 pgs.
"U.S. Appl. No. 12/701,228, Notice of Allowance mailed Jun. 27, 2011", 5 pgs.
"U.S. Appl. No. 13/017,354, Non Final Office Action mailed Jan. 9, 2012", 8 pgs.
"U.S. Appl. No. 13/017,354, Non Final Office Action mailed Jun. 24, 2011", 8 pgs.
"U.S. Appl. No. 13/017,354, Notice of Allowance mailed Jul. 24, 2012", 7 pgs.
"U.S. Appl. No. 13/017,354, Response filed Jul. 5, 2012 to Non Final Office Action mailed Jan. 9, 2012", 15 pgs.
"U.S. Appl. No. 13/017,354, Response filed Sep. 26, 2011 to Non-Final Office Action mailed Jun. 24, 2011", 16 pgs.
"U.S. Appl. No. 13/285,551, Non Final Office Action mailed Apr. 12, 2012", 5 pgs.
"U.S. Appl. No. 13/285,551, Notice of Allowance mailed Nov. 5, 2012", 7 pgs.
"U.S. Appl. No. 13/285,551, Response filed Oct. 12, 2012 to Non Final Office Action mailed Apr. 12, 2012", 8 pgs.
"U.S. Appl. No. 13/685,048, Non Final Office Action mailed Aug. 29, 2013", 10 pgs.
"U.S. Appl. No. 13/779,985 , Response filed Sep. 25, 2013 to Non Final Office Action mailed Apr. 25, 2013", 12 pgs.
"U.S. Appl. No. 13/779,985, Non Final Office Action mailed Apr. 25, 2013", 7 pgs.
"U.S. Appl. No. 13/779,985, Notice of Allowance mailed Jan. 9, 2014", 16 pgs.
"Canadian Application Serial No. 2,348,580, Office Action mailed Feb. 20, 2007", 2 pgs.
"Canadian Application Serial No. 2,348,580, Response filed Aug. 16, 2007 to Office Action mailed Feb. 20, 2007", 7 pgs.
"Canadian Application Serial No. 2,501,048, Office Action mailed Aug. 26, 2013", 2 pgs.
"Canadian Application Serial No. 2,501,048, Office Action mailed Nov. 29, 2011", 3 pgs.
"Canadian Application Serial No. 2,501,048, Office Action mailed Jun. 4, 2012", 3 pgs.
"Canadian Application Serial No. 2,501,048, Response filed Dec. 4, 2012 to Office Action mailed Jun. 4, 2012", 17 pgs.
"Canadian Application Serial No. 2,630,662, Office Action mailed Sep. 6, 2013", 3 pgs.
"Canadian Application Serial No. 2501048, Response filed May 8, 2012 to Office Action mailed Nov. 29, 2011", 11 pgs.
"European Application Serial No. 03756904.3 , Amendment filed Feb. 13, 2012 to Office Action mailed Aug. 1, 2011", 17 pp.
"European Application Serial No. 03756904.3 , Office Action mailed Aug. 1, 2011", 4 pgs.
"European Application Serial No. 03756904.3 Amendment filed May 13, 2010 to Office Action mailed Nov. 3, 2009", 23 pp.
"European Application Serial No. 03756904.3 Office Action mailed Nov. 3, 2009", 2 pgs.
"European Application Serial No. 05024287, Search Report mailed Dec. 16, 2005", 3 pgs.
"European Application Serial No. 05024287.4, Office Action mailed Sep. 25, 2012", 1 pg.
"European Application Serial No. 05024287.4, Office Action mailed Feb. 9, 2012", 4 pgs.
"European Application Serial No. 05024287.4, Response filed Nov. 23, 2012 to Office Action mailed Sep. 25, 2012", 9 pgs.
"European Application Serial No. 05024287.4, Response filed Jun. 6, 2007 to Office Action mailed Sep. 22, 2006", 8 pgs.
"European Application Serial No. 05024287.4, Search Report mailed Jan. 3, 2006", 7 pp.
"European Application Serial No. 06838195.3—Office Action Received mailed Dec. 7, 2012", 7 pgs.
"European Application Serial No. 06838195.3, Office Action mailed Jul. 27, 2009", 4 pgs.
"European Application Serial No. 06838195.3, Response filed Feb. 4, 2010 to Office Action mailed Jul. 27, 2009", 8 pgs.
"European Application Serial No. 06838195.3, Response filed Jan. 15, 2013 to Office Action mailed Dec. 7, 2012", 1 pg.
"European Application Serial No. 09793238.8, Amendment Filed Apr. 29, 2011", 19 pp.
"European Application Serial No. 99950325.3, Communication dated Jul. 28, 2004", 5 pgs.
"European Application Serial No. 99950325.3, European Search Report Mailed Mar. 8, 2004", 3 pp.
"European Application Serial No. 99950325.3, Examination Report Mailed Jul. 28, 2004", 3 pp.
"European Application Serial No. 99950325.3, Response filed Feb. 7, 2005 to European Search Report Mailed Mar. 8, 2004", 10 pp.
"European Application Serial No. 99950325.3, Response filed Feb. 7, 2005 to Official Action mailed Jul. 28, 2004", 11 pp.
"International Application Serial No. PCT/US03/31280 International Search Report mailed Jul. 19, 2004", 5 pgs.

(56) References Cited

OTHER PUBLICATIONS

"International Application Serial No. PCT/US03/31280, Preliminary Examination Report mailed Feb. 1, 2005", 16 pgs.
"International Application Serial No. PCT/US2003/031280, Response filed Jan. 19, 2005 to Written Opinion mailed Jan. 14, 2005", 14 pgs.
"International Application Serial No. PCT/US2003/031280, Written Opinion mailed Jan. 14, 2005", 7 pgs.
"International Application Serial No. PCT/US2006/045080, Partial International Search Report mailed Mar. 9, 2007", 3 pgs.
"International Application Serial No. PCT/US2006/045080, Search Report and Written Opinion mailed May 16, 2007", 16 Pages.
"International Application Serial No. PCT/US2009/059218, International Preliminary Report on Patentability mailed Apr. 5, 2011", 9 pgs.
"International Application Serial No. PCT/US2009/059218, International Search Report mailed Feb. 12, 2010", 3 pgs.
"International Application Serial No. PCT/US2009/059218, Written Opinion mailed Apr. 2, 2011", 8 pgs.
"Japanese Application Serial No. 2000-547913, Argument and Amendment filed May 22, 2009 to Office Action mailed Feb. 24, 2009", (w/ English Translation of Amended Claims), 9 pgs.
"Japanese Application Serial No. 2000-547913, Argument and Amendment filed Dec. 18, 2009 to Office Action mailed Jun. 23, 2009", (w/ English Translation of Amended Claims), 13 pgs.
"Japanese Application Serial No. 2000-547913, Office Action mailed Feb. 24, 2009", (w/ English Translation), 7 pgs.
"Japanese Application Serial No. 2000-547913, Office Action mailed Jun. 23, 2009", (w/ English Translation), 8 pgs.
"Japanese Application Serial No. 2004-543092, Response filed Nov. 15, 2010 to Office Action mailed Jul. 13, 2010", (w/ English Translation), 24 pp.
"Japanese Application Serial No. 2004-543092, Office Action mailed Jul. 13, 2010", (w/ English Translation), 2 pgs.
"Japanese Application Serial No. 2004-543092, Office Action mailed Nov. 17, 2009", (w/ English Translation), 12 pgs.
"Japanese Application Serial No. 2004-543092, Response filed May 17, 2010 to Office Action mailed Nov. 17, 2009", Japanese only, 18 pp.
"Japanese Application Serial No. 2008-541424, Office Action mailed Sep. 3, 2013", w/English translation, 6 pgs.
"Japanese Application Serial No. 2008-541424, Office Action mailed Oct. 30, 2012", (w/ English Translation), 8 pgs.
"Japanese Application Serial No. 2010-113577—Office Action Received Aug. 14, 2012", (w/ English Translation), 6 pgs.
"Japanese Application Serial No. 2010-113577—Response filed Feb. 14, 2013 to Office Action Received Aug. 14, 2012", Japanese only, 8 pgs.
"Japanese Application Serial No. 2010-113577, Office Action mailed Feb. 14, 2012", With English Translation, 6 pgs.
"Japanese Application Serial No. 2010-113577, Response filed May 2, 2012 to Office Action mailed Feb. 14, 2012", with English claims, 9 pgs.
"Japanese Application Serial No. 2004-543092, Notice of Allowance mailed Apr. 5, 2011", (w/ English Translation), 1 page.
"Optical Review", vol. 4 .No. 6, (Nov / Dec 1997), 1 pg.
"Tissue Characterization through Ultrasonic Backscatter", [online] [retrieved Sep. 25, 2002]., Retrieved via the Internet: <URL: http://www.brl.uiuc.edu/Projects/backscatter.htm>, 5 pgs.
Bates, K. N., "A High Acuity 3D Acoustic Imaging System", Proceedings., 1995 IEEE Ultrasonics Symposium, 2, (Nov. 7-10, 1995), 1245-1250.
Bates, K. N., "A One Dimensional Phased Array Imaging System", Ph.D. Dissertation, Applied Physics, Stanford University, (1982), 186 pgs.
Bates, K. N., et al., "PEOATS and ESOATS", IEEE Ultrasonics Symposium Proceedings, 1979, (Sep. 26-28, 1979), 189-194.
Bates, K. N., "Tolerance Analysis for Phased Arrays", Acoustic Imaging, 9, (1980), 239-262.
Bates, Kenneth N, "A high acuity 3-D acoustic imaging system", Proceedings., 1995 IEEE Ultrasonics Symposium, 2, (Nov. 7-10, 1995), 1245-1250.
Bates, Kenneth N., et al., "Digitally Controlled Electronically Scanned and Focused Ultrasonic Imaging System", IEEE Ultrasonics Symposium Proceedings, 1979, (Sep. 26-28, 1979), 216-220.
Blotekjaer, K., "Theoretical concepts of a novel Vernier-based fringe-counting fibre optic sensor", IEE Proceedings, Optoelectronics, 144(3), (Jun. 1997), 126-129.
Brady, G. P, et al., "Simultaneous measurement of strain and temperature using the first- and second-order diffraction wavelengths of Bragg gratings", IEE Proceedings, Optoelectronics, 144(3), (Jun. 1997), 156-161.
Buma, T., et al., "A high frequency ultrasound array element using thermoelastic expansion in PDMS", Proceedings of the 2001 IEEE Ultrasonics Symposium, 2, (Oct. 7-10, 2001), 1143-1146.
Buma, T., et al., "A high-frequency, 2-D array element using thermoelastic expansion in PDMS", IEEE Transactions on Ultrasonics, Ferroelectrics and Frequency Control, 50(9), (Sep. 2003), 1161-1176.
Buma, T., et al., "High Frequency Ultrasonic Imaging Using Optoacoustic Arrays", Proceedings of the Proceeding of the 2002 IEEE Ultrasonics Symposium, 1, Invited paper, (Oct. 8-11, 2002), 571-580.
Buma, T., et al., "High Frequency Ultrasound Array Element using Thermoelastic Expansion in an Elastomeric Film", Applied Physics Letters, 79(4), (Jul. 23, 2001), 548-550.
Buma, T., et al., "High-frequency ultrasound imaging using optoacoustic arrays", Proceedings of the SPIE—The International Society for Optical Engineering, 4687, (2002), 99-109.
Buma, T., et al., "Thermoelastic Expansion versus Piezoelectricity for High Frequency 2-D Arrays", IEEE Transactions on Ultrasonics, Ferroelectrics and Frequency Control, 50(8), (Aug. 2003), 1065-1068.
Buma, T., et al., "Thermoelastic Generation of Continuous Lamb Waves for Microfluidic Devices", Proceeding of the 2003 IEEE Ultrasonics Symposium, (2003), 150-153.
Buma, T., et al., "Thermoelastic Generation of Ultrasound Using anErbium Doped Fiber Amplifier", Proceeding of the 1999 IEEE Ultrasonics Symposium, 2, (Oct. 17-20, 1999), 1253-1256.
Davis, M. A, et al., "Simultaneous measurement of temperature and strain using fibre Bragg gratings and Brillouin scattering", IEE Proceedings, Optoelectronics, 144(3), (Jun. 1997), 151-155.
Feced, R., et al., "Advances in high resolution distributed temperature sensing using the time-correlated single photon counting technique", IEE Proceedings, Optoelectronics, 144(3), (Jun. 1997), 183-188.
Furstenau, N., et al., "Extrinsic Fabry-Perot interferometer vibration and acoustic sensor systems for airport ground traffic monitoring", IEE Proceedings, Optoelectronics, 144(3), (Jun. 1997), 134-144.
Hamilton, J. D., et al., "An active optical detector for high frequency ultrasound imaging", Proceedings of the 1997 IEEE Ultrasonics Symposium, 1, (Oct. 5-8, 1997), 753-756.
Hamilton, J. D., et al., "High frequency optoacoustic arrays using etalon detection", IEEE Transactions on Ultrasonics, Ferroelectrics and Frequency Control, 47(1), (Jan. 2000), 160-169.
Hamilton, J. D., et al., "High Frequency Ultrasound Imaging Using an Active optical Detector", IEEE Transactions on Ultrasonics, Ferroelectrics and Frequency Control UFFC-45, (1998), 719-727.
Hamilton, J. D., et al., "High Frequency Ultrasound Imaging with Optical Arrays", IEEE Transactions on Ultrasonics, Ferroelectrics and Frequency Control, 45(1), (Jan. 1998), 216-235.
Hamilton, J. D., et al., "Optical Arrays for High Frequency Ultrasound Imaging", Proceedings of the 1996 IEEE Ultrasonics Symposium, (1996), 1419-1422.
Karl, W Clem, "Multi-Sensor Fusion for Atherosclerotic Plaque Characterization", Boston University—MDSP, obtained from the internet on Sep. 25, 2002, [Online] Retrieved from the internet:<http://www.censsis.neu/Education/StudentResearch/2001/posters/weisensell)r!.pdf>, 15 pgs.
Komiyama, N., et al., "Tissue Characterization of Atherosclerotic Plaques by Intravascular Ultrasound Radiofrequency Signal Analysis: An in Vitro Study of Human Coronary Arteries", Entrez-

(56) References Cited

OTHER PUBLICATIONS

PubMed—(http://www.ncbi.nlm.nih.gov/entrez/query)—viewed web site on Sep. 25, 2002, pp. 1-2.
Krass, S., et al., "P3.4 Pattern Recognition Algorithms for Tissue Characterization in Intracoronary Ultrasound Imaging: Test Data Set and Results of Computerized Texture Analysis", 2nd Medical Clinic, Univ-Mainz, Germany—, (http://www.uni-mainz.de/Cardio/incis/Data/p3_4.htm)—view web site on Sep. 25, 2002, pp. 1-3.
Lockey, R. A, et al., "Multicomponent time-division-multiplexed optical fibre laser Doppler anemometry", IEE Proceedings, Optoelectronics, 144(3), (Jun. 1997), 168-175.
MacPherson, W. N, et al., "Phase demodulation in optical fibre Fabry-Perot sensors with inexact phase steps", IEE Proceedings, Optoelectronics, 144(3), (Jun. 1997), 130-133.
McCulloch, S., et al., "Development of a fibre optic micro-optrode for intracellular pH measurements", IEE Proceedings, Optoelectronics, 144(3), (Jun. 1997), 162-167.
Mintz, Gary S., et al., "American College of Cardiology Clinical Expert Consensus Document on Standards for Acquisition, Measurement and Reporting of Intravascular Ultrasound Studies (IVUS)", Journal of the American College of Cardiology, 37(5), (Apr. 2001), 1478-1492.
Moreira, P J, et al., "Dynamic Range Enhancement in Fiber Bragg Grating Sensors using a Multimode Laser Diode", IEEE Photonics Technology Letters, vol. 11, No. 6, (Jun. 1999), 3 pgs.
O'Donnell, M., "New Imaging Technologies for Ultrasonography", J Med Ultrason., 27(4), Presented at the 73rd Japan Society of Ultrasound in Medicine Meeting, Invited Paper, (2000), 356-357.
O'Donnell, M., et al., "Optoacoustics: high frequency ultrasonic array imaging", Proceedings of 17th International Congress on Acoustics, vol. IV, Biomedicine, Acoustics in Medicine, Invited Presentation at the 17th Intl Congress on Acoustics, Rome, (Sep. 2-7, 2001), 2-3.
Othonos, A., et al., "In Section 7.9 Bragg Gating Fiber Laser Sensors from Fiber Bragg Gratings: fundamentals and applications in telecommunications and sensing", (1999 Artech House, Inc.), (1999), 355-367.
Pepine, Carl J., et al., "Improving Diagnostic and Therapeutic Outcomes Through Advanced Intravascular Imaging", Vascular Technologies, Inc., (1989), 3 pgs.
Scully, P. J., "UV Laser Photo-induced Refractive Index Changes in Poly-Methyl-Meth-Acrylate and Plastic Optical Fibres for Application as Sensors and Devices", Central Laser Facility Annual Report, 1999/2000, (1999-2000), 145-147.
Spisar, M., et al., "Stabilized, Resonant Optoacoustic Array Detectors for Medical Imaging", Proceedings of the World Congress on Ultrasonics, Paris, France, (Sep. 7-10, 2003), 25-28.
Stefanadis, Christodoulos, et al., "Identification and Stabilization of Vulnerable Atherosclerotic Plaques: The Role of Coronary Thermagraphy and External Heat Delivery", Identification and Stabilization of Vulnerable Atherosclerotic Plaques IHJ—(viewed web site on Sep. 25, 2002), http://www.indianheartjournal.org, (2001), 1-10.
Surowiec, J., et al., "A Novel Miniature Optical Fibre Probe for MHz Frequency Ultrasound", Proceedings, IEEE Ultrasonics Symposium, vol. 2, (Nov. 3-6, 1996, San Antonio, TX), (1996), 1051-1054.
Takahashi, N., et al., "Underwater Acoustic Sensor with Fiber Bragg Grating", Optical Review, 4(6), (1997), 691-694.
Tanaka, S., et al., "Fibre optic spectral polarimetry for sensing multiple stress-loaded locations along a length of fibre", IEE Proceedings, Optoelectronics, 144(3), (Jun. 1997), 176-182.
Wahle, Andreas, et al., "Accurate Visualization and Quantification of Coronary Vasculature by 3-D/4-D Fusion from Biplane Angiography and Intravascular Ultrasound", in: Biomonitoring and Endoscopy Technologies; I. Gannot et al., eds, (Jul. 5-6, 2000), 144-155.
Yoshino, T., et al., "Spiral fibre microbend sensors", IEE Proceedings, Optoelectronics, 144(3), (Jun. 1997), 145-150.
U.S. Appl. No. 12/020,736, Advisory Action mailed Feb. 13, 2014, 3 pgs.
U.S. Appl. No. 12/020,736, Examiner Interview Summary mailed May 8, 2014, 3 pgs.
U.S. Appl. No. 12/020,736, Notice of Allowance mailed Aug. 29, 2014, 9 pgs.
U.S. Appl. No. 12/020,736, Response filed Mar. 13, 2014 to Advisory Action mailed Feb. 13, 2014, 14 pgs.
U.S. Appl. No. 12/020,736, Supplemental Response filed May 16, 2014 to Final Office Action mailed Oct. 25, 2013, 13 pgs.
U.S. Appl. No. 14/280,327, Preliminary Amendment field Jun. 6, 2014, 6 pgs.
Canadian Application Serial No. 2,501,048, Office Action mailed Jul. 8, 2014, 2 pgs.
Canadian Application Serial No. 2,501,048, Response filed Feb. 11, 2014 to Office Action mailed Aug. 26, 2013, 10 pgs.
European Application Serial No. 03756904.3, Office Action mailed May 31, 2013, 2 pgs.
European Application Serial No. 03756904.3, Response filed Oct. 10, 2013 to Office Action mailed May 31, 2013, 17 pgs.
European Application Serial No. 05024287.4, Examination Notification Art. 94(3) mailed Apr. 25, 2014, 4 pgs.
European Application Serial No. 05024287.4, Office Action mailed Sep. 22, 2006, 1 pg.
International Application Serial No. PCT/US03/31280, Demand and Response filed May 6, 2004 to Partial Search Report mailed Dec. 2, 2004, 13 pgs.
International Application Serial No. PCT/US03/31280, Invitation to Pay Additional Fees and Partial Search Report mailed Feb. 12, 2004, 10 pgs.
International Application Serial No. PCT/US99/04913, International Search Report mailed May 28, 1999, 1 pg.
Japanese Application Serial No. 2010-113577, Amendment filed Nov. 15, 2010, w/English claims, 16 pgs.
Application Serial No. 14/280,327, Notice of Allowance mailed Jan. 27, 2015, 7 pgs.
Siebes, M., et al., "Single-Wire Pressure and Flow Velocity Measurement to Quantify Coronary Stenosis Hemodynamics and Effects of Percutaneous Interventions", Circulation, 109, (2004), 756-762.

* cited by examiner

OPTICAL ULTRASOUND RECEIVER

CLAIM OF PRIORITY

This patent application is a continuation application of U.S. patent application Ser. No. 12/571,724, filed on Oct. 1, 2009, now U.S. Pat. No. 8,560,048, issued on Oct. 15, 2013, which claims the benefit of priority of Michael J. Eberle et al. U.S. Provisional Patent Application Ser. No. 61/102,216, which was filed on Oct. 2, 2009, the entire content of each being incorporated herein by reference in its entirety, and the benefit of priority of each is claimed herein.

BACKGROUND

Bates et al. U.S. Pat. No. 7,245,789 is incorporated by reference herein in its entirety, including its discussion of systems and methods for minimally-invasive optical-acoustic imaging. It discusses, among other things, an imaging guidewire that includes one or more optical fibers communicating light along the guidewire. At or near a distal end of the guidewire, light is directed to a photoacoustic transducer material that provides ultrasonic imaging energy. Returned ultrasound energy is sensed by an ultrasound-to-optical transducer. A responsive signal is optically communicated to the proximal end of the guidewire, such that it can be processed to develop a 2D or 3D image.

Overview

Among other things, the present applicant has recognized the desirability of reducing or minimizing the size of a system like that described in Bates. However, the present applicant has recognized that reducing the size of the ultrasound-to-optical transducer can also change the mechanical acoustic resonance of the transducer at some ultrasound frequencies and can also result in a generally smaller output signal. Additionally, the transducer response can become dependent on the polarization of the optical signal since it is responsive to acoustic impedances in the direction of polarization. This can result in undesirable variations in the output signal conditional on the polarization direction due to different resonances in different lateral directions, for example. One approach to reduce or eliminate this effect would be to control polarization of the optical signal. However, such polarization is difficult to control or predict in a cost-effective manner. Accordingly, the present applicant has recognized, among other things, that it can be advantageous to provide an ultrasound-to-optical transducer that is relatively insensitive to optical signal polarization.

Example 1 can include an ultrasound-to-optical transducer, including an optical fiber, an ultrasound-absorptive backing configured for substantially absorbing ultrasound energy that passes beyond the optical fiber to reach the backing, and a Fiber Bragg Grating (FBG) interferometer configured for receiving the ultrasound energy and capable of modulating an optical sensing signal, in response to the ultrasound energy, substantially independent of a polarization angle of the optical sensing signal. In this example, the optical fiber can include an optical fiber diameter that is less than half of a wavelength of target ultrasound energy to be received by the transducer.

In Example 2, the subject matter of Example 1 can optionally comprise an elongated intravascular imaging assembly, comprising a proximal external portion comprising an optical signal interface and a distal portion sized and shaped and configured for internal intravascular acoustic imaging. In this example, the imaging assembly can comprise an elongated support, extending substantially from the proximal portion of the imaging assembly to the distal portion of the imaging assembly, the support configured to provide adequate length, rigidity, and flexibility to permit intravascular introduction and steering of a distal portion of the imaging assembly to a location of interest, the optical fiber, extending longitudinally and affixed along the support substantially from the proximal portion of the imaging assembly substantially to the distal portion of the imaging assembly, a transducer, located at or near a distal portion of the imaging assembly and configured as at least one of the ultrasound-to-optical transducer or an optical-to-ultrasound transducer; and the backing, located in a backing region between the transducer and the elongated support, the backing configured to attenuate ultrasound energy that reaches the backing region by at least 90%.

In Example 3, the subject matter of any one of Examples 1 or 2 can optionally be configured so that the assembly comprises a plurality of the optical fibers, extending longitudinally and affixed along the support, the fibers arranged circumferentially about a central longitudinal axis of the support, and a plurality of the transducers, wherein the transducer includes a photoacoustic material located at a peripheral portion of the optical fiber that is away from the backing.

In Example 4, the subject matter of any one of Examples 1-3 can optionally be configured such that the optical fiber diameter is less than sixty micrometers.

In Example 5, the subject matter of any one of Examples 1-4 can optionally be configured so that the backing comprises microballoons containing a gas.

In Example 6, the subject matter of any one of Examples 1-5 can optionally be configured so that the microballoons comprise about 30% to about 50% of the volume of the backing.

In Example 7, the subject matter of any one of Examples 1-6 can optionally be configured so that a thickness of the backing is between about 25 micrometers and about 100 micrometers.

In Example 8, the subject matter of any one of Examples 1-7 can optionally comprise the transducer being configured such that a peak-to-peak amplitude of an oscillating output optical bias signal modulated by the transducer varies by no more than one decibel when the polarization angle of the optical sensing signal is varied by 90 degrees.

In Example 9, the subject matter of any one of Examples 1-8 can optionally be configured such that a total birefringence induced on an optical signal with a wavelength of about 1550 nanometers transmitted within the optical fiber is less than $(3 \times 10^{-6})$.

Example 10 can include (or can be combined with the subject matter of any one of Examples 1-9 to include) fabricating an ultrasound-to-optical transducer, the fabricating comprising providing an optical fiber that includes a diameter that is less than half of a wavelength of target ultrasound energy to be received by the transducer, creating a Fiber Bragg Grating (FBG) interferometer configured for receiving the ultrasound energy and capable of modulating an optical sensing signal substantially independent of a polarization of the optical sensing signal, associating an ultrasound-absorptive backing with the optical fiber, and configuring the backing for substantially absorbing ultrasound energy that passes beyond the optical fiber to reach the backing.

In Example 11, the subject matter of any one of Examples 1-10 can optionally comprise associating the backing comprising microballoons containing a gas with the fiber.

In Example 12, the subject matter of any one of Examples 1-11 can optionally comprise providing the backing comprising the microballoons that comprise about 30% to about 50% of the volume of the backing.

In Example 13, the subject matter of any one of Examples 1-12 can optionally comprise inserting the backing into a backing region between a central support structure and the optical fiber, wherein both the support structure and the fiber extend longitudinally, the backing region being bounded laterally by a tubular sheath.

In Example 14, the subject matter of any one of Examples 1-13 can optionally comprise conforming the backing to the external surface of a central support structure, wherein both the support structure and the fiber extend longitudinally.

In Example 15, the subject matter of any one of Examples 1-14 can optionally further comprise conforming a tubular sheath to a surface of the backing that is away from the support structure.

Example 16 can include (or can be combined with the subject matter of any one of Examples 1-15 to include) receiving ultrasound energy with an optical fiber, the optical fiber including a diameter that is less than half of a wavelength of the ultrasound energy, and using the ultrasound energy to modulate an optical sensing signal substantially independent of a polarization of the optical sensing signal.

In Example 17, the subject matter of any one of Examples 1-16 can optionally comprise using the ultrasound energy to modulate the optical sensing signal substantially independent of the polarization of the optical sensing signal comprises generating a modulated output optical signal with a peak-to-peak amplitude that varies by no more than one decibel when a polarization angle of the optical sensing signal is varied by 90 degrees.

In Example 18, the subject matter of any one of Examples 1-17 can optionally comprise using an ultrasound-absorptive backing to substantially attenuate ultrasound energy that passes beyond the optical fiber to reach the backing.

In Example 19, the subject matter of any one of Examples 1-18 can optionally comprise using the ultrasound-absorptive backing to attenuate ultrasound energy that passes beyond the optical fiber to reach the backing by at least 90%.

In Example 20, the subject matter of any one of Examples 16-19 can optionally comprise forming an image of a region within a living body using information from a modulated output optical signal.

These examples can be combined with each other in any permutation or combination and or with other subject matter disclosed herein. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

1. Examples of Fiber Bragg Grating Strain Sensors

Figure 1:
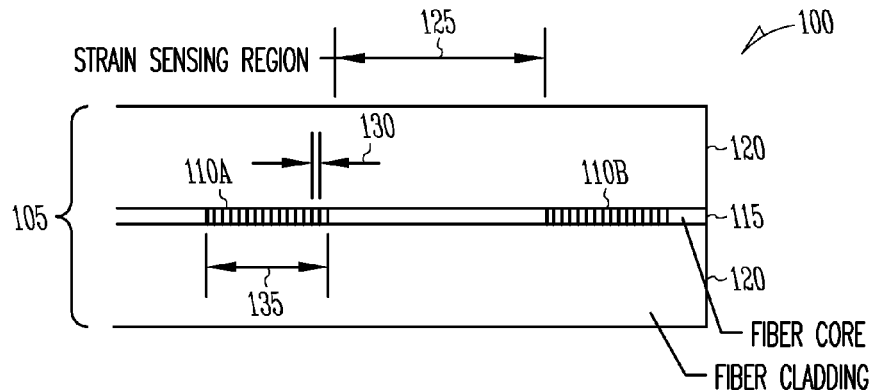
FIG. 1 is a cross-sectional side view illustrating generally, by way of example, but not by way of limitation, an example of an FBG strain sensor in an optical fiber.

FIG. 1 is a cross-sectional side view illustrating generally, by way of example, but not by way of limitation, an example of a strain-detecting or pressure-detecting acoustic-to-optical FBG sensor 100 in an optical fiber 105. FBG sensor 100 senses acoustic energy received from a nearby area to be imaged, and transduces the received acoustic energy into an optical signal within optical fiber 105. In the example of FIG. 1, FBG sensor 100 can include Bragg gratings 110A-B in an optical fiber core 115, such as surrounded by an optical fiber cladding 120. Bragg gratings 110A-B can be separated by a strain or pressure sensing region 125, which, in an example, can be about a millimeter in length. This example can sense strain or pressure such as by detecting a variation in length of the optical path between these gratings 110A-B.

A Fiber Bragg Grating can be conceptualized as a periodic change in the optical refractive index of a portion of the optical fiber core 115. Light of specific wavelengths traveling down such a portion of core 115 will be reflected; the period (distance) 130 of the periodic change in the optical index determines the particular wavelengths of light that will be reflected. The degree of optical index change and the length 135 of the grating determine the ratio of light reflected to that transmitted through the grating 110A-B.

Figure 2:
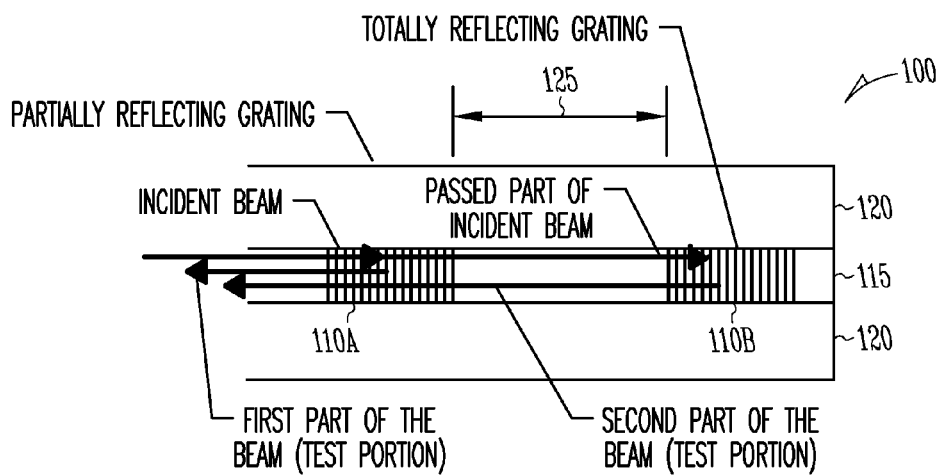
FIG. 2 is a cross-sectional side view illustrating generally, by way of example, but not by way of limitation, an example of an FBG grating interferometer sensor.

FIG. 2 is a cross-sectional side view illustrating generally, by way of example, but not by way of limitation, an operative example of an interferometric FBG sensor 100. The example of FIG. 2 can include two FBG mirrors 110A-B, which can be both partially reflective such as for a specific range of wavelengths of light passing through fiber core 115. Generally, the reflectivity of each FBG will be substantially similar, but can differ for particular implementations. This interferometric arrangement of FBGs 110A-B can be capable of discerning the "optical distance" between FBGs 110A-B with extreme sensitivity. The "optical distance" can be a function of the effective refractive index of the material of fiber core 115 as well as the length 125 between FBGs 110A-B. Thus, a change in the refractive index can induce a change in optical path length, even though the physical distance 125 between FBGs 110A-B has not substantially changed.

An interferometer, such as FBG sensor 100, can be conceptualized as a device that measures the interference between light reflected from each of the partially reflective FBGs 110A-B. When the optical path length between the FBG mirrors 110A-B is an exact integer multiple of the wavelength of the optical signal in the optical fiber core 115, then the light that passes through the FBG sensor 100 will be a maximum and the light reflected will be a minimum, so the optical signal is substantially fully transmitted through the FBG sensor 100. This addition or subtraction can be conceptualized as interference. The occurrence of full transmission or minimum reflection can be called a "null" and occurs at a precise wavelength of light for a given optical path length. Measuring the wavelength at which this null occurs can yield an indication of the length of the optical path between the two partially reflective FBGs 110A-B. In such a manner, an interferometer, such as FBG sensor 100, can sense a small change in distance, such as a change in the optical distance 125 between FBGs 110A-B resulting from received ultrasound or other received acoustic energy. This arrangement can be thought of as a special case of the FBG Fabry-Perot interferometer, sometimes more particularly described as an Etalon, because the distance 125 between the FBGs 110A-B is substantially fixed.

The sensitivity of an interferometer, such as FBG sensor 100, can depend in part on the steepness of the "skirt" of the null in the frequency response. The steepness of the skirt can be increased by increasing the reflectivity of the FBGs 100A-B, which also increases the "finesse" of the interferometer. The present applicant has recognized, among other things, that increasing the finesse or steepness of the skirt of FBG sensor 100 can increase the sensitivity of the FBG sensor 100 to the reflected ultrasound signals within a particular wavelength range but can decrease the dynamic range. As such, keeping the wavelength of the optical sensing signal within the wavelength range can be advantageous. In an example, a closed-loop system can monitor a representative wavelength (e.g., the center wavelength of the skirt of the filtering FBG sensor 100) and can adjust the wavelength of an optical output laser to remain substantially close to the center of the skirt of the filter characteristic of the FBG sensor 100 as forces external to the optical fiber 105, such as bending and stress, cause the center wavelength of the skirt of the filter characteristic of the FBG sensor 100 to shift.

In an example, such as illustrated in FIG. 2, the interferometric FBG sensor 100 can cause interference between that portion of the optical beam that is reflected off the first partially reflective FBG 110A with that reflected from the second partially reflective FBG 110B. The wavelength of light where an interferometric null will occur can be very sensitive to the "optical distance" between the two FBGs 110A-B. The interferometric FBG sensor 100 of FIG. 2 can provide another very practical advantage. In this example, the two optical paths along the fiber core 115 are the same, except for the sensing region between FBGs 110A-B. This shared optical path ensures that any optical changes in the shared portion of optical fiber 105 will have substantially no effect upon the interferometric signal; only the change in the sensing region 125 between FBGs 110A-110B is sensed. However, the present applicant has recognized, among other things, that this sensing can be affected by birefringence of the optical fiber within FBG sensor 100.

Optical birefringence is a measure of the difference in refractive index of an optical medium for light of different polarizations. The polarization of light can be defined as the orientation of the electric vector of the electromagnetic light wave. Birefringence between two at least partially reflective FBGs, such FBGs 110A-B, can cause different beams of light with different polarizations to effectively travel slightly different optical path lengths between the FBGs 110A-B. Therefore, a combination of birefringence between the at least partially reflective FBGs 110A-B and a shift in the polarization of the optical signal within the optical fiber core 115 can cause a shift in the exact wavelength of the null of the FBG sensor 100. When light is split between different polarization states, the light will be reflected or transmitted from different parts of the skirt of the null, which can lead to fading of the optically transduced signal. There are many possible states of polarization, such as linear, circular, and elliptical, but the worst signal fading generally occurs when the optical signal is split equally between linear polarization states that are orthogonally aligned. With this in mind, the present applicant has recognized, among other things, that birefringence should be reduced or otherwise addressed, if possible.

The present applicant has also recognized that there can be two main sources of optical birefringence within the FBG sensor 100. The first source is the intrinsic birefringence of the optical fiber 105. The intrinsic birefringence is determined mostly during the manufacturing of the optical fiber 105 and is generally a function of the level of geometric symmetry, the uniformity of dopant distribution, and the level of stress in the fiber core 115 during the drawing of the fiber core 115.

The second source of optical birefringence in the FBG sensor 100 is the process of writing the FBGs 110A and 110B. The present applicant has also recognized that the birefringence induced by the writing of FBGs 110A and 110B can be reduced such as by controlling one or more aspects of the writing process, such as the polarization of the writing laser, the laser pulse energy, the writing exposure time, the amount of hydrogen or deuterium in the fiber during writing, or any combination thereof.

2. Examples of FBG Acoustic-to-Optical Transducers

In an example, an FBG sensor 100 senses pressure or strain such as generated by ultrasound or other acoustic energy received from a nearby imaging region to be visualized and, in response, modulates an optical sensing signal in an optical fiber. Increasing the sensitivity of the FBG sensor 100 can provide improved imaging. A first example of increasing sensitivity is to increase the amount of strain induced in the FBG sensor 100 for a given dynamic pressure provided by the acoustic energy. A second example is to increase the modulation of the optical signal for a given change in strain of the FBG sensor 100. Any combination of the techniques of these first and second examples can also be used.

Figure 3:
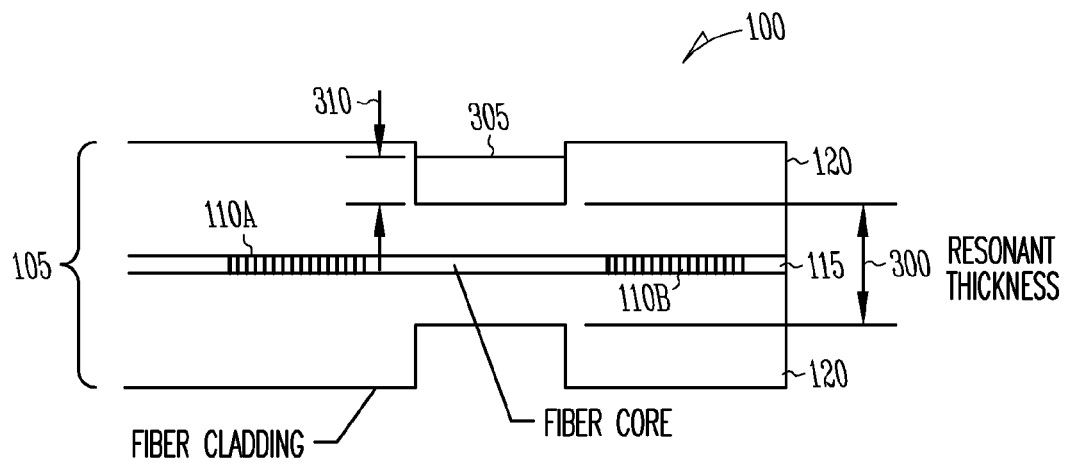
FIG. 3 is a cross-sectional schematic diagram illustrating generally an example of an acousto-optic transducer.

One technique of increasing the strain induced in the FBG sensor 100 is to configure the physical attributes of the FBG sensor 100 such as to increase the degree of strain for a given externally-applied acoustic field. In an example, the FBG sensor 100 can be shaped so as to increase the strain for a given applied acoustic pressure field. FIG. 3 is a cross-sectional schematic diagram illustrating such an example in which the FBG sensor 100 is shaped such that it mechanically resonates at or near the frequency of the acoustic energy received from the nearby imaging region, thereby resulting in increased strain. In the example of FIG. 3, all or a portion of the strain sensing region between FBGs 110A-B is selected to provide a thickness 300 that promotes such mechanical resonance of the received acoustic energy, thereby increasing the resulting strain sensed by FBG sensor 100. In an example, such as illustrated in FIG. 3, this can be accomplished by grinding or otherwise removing a portion of fiber cladding 120, such that the remaining thickness of fiber core 115 or fiber cladding 120 between opposing planar (or other) surfaces is selected to mechanically resonate at or near the frequency of the acoustic energy received from the nearby imaging region.

In an example, mechanical resonance can be obtained by making the thickness 300 of the strain sensing region substantially the same thickness as ½ the acoustic wavelength (or an odd integer multiple thereof) in the material(s) of FBG sensor 100 at the acoustic center frequency of the desired acoustic frequency band received from the imaging region. In other examples, such as for other materials, the thickness 300 can be selected to match a different proportion of the acoustic wavelength that obtains the desired mechanical resonance for that material. Calculations indicate that obtaining such mechanical resonance can increase the strain sensitivity by a factor of 2 or more over that of a sensor that is not constructed to obtain such mechanical resonance.

In a third example, a coating 305 can be applied to the FBG sensor 100 such as to increase the acoustic pressure as seen by the FBG sensor 100 over a band of acoustic frequencies, such as for improving its sensitivity over that band. The difference between the mechanical characteristics of water (or tissue and/or blood, which is mostly comprised of water) and glass material of the optical fiber 105 carrying the FBG sensor 100 is typically so significant that only a small amount of acoustic energy "enters" the FBG sensor 100 and thereby causes strain; the remaining energy is reflected back into the biological or other material being imaged. For a particular range of acoustic frequencies, one or more coatings 305 of specific thickness 310 or mechanical properties (e.g., the particular mechanical impedance) of the coating material can be used to dramatically reduce such attenuation due to the different mechanical characteristics. An example can use quarter wave matching, providing a coating 305 of a thickness 310 that is approximately equal to one quarter of the acoustic signal wavelength received from the region being imaged. Using such matching, the sensitivity of the FBG sensor 100, over a given band of acoustic frequencies of interest, is expected to increase by about a factor of 2.

Figure 4:
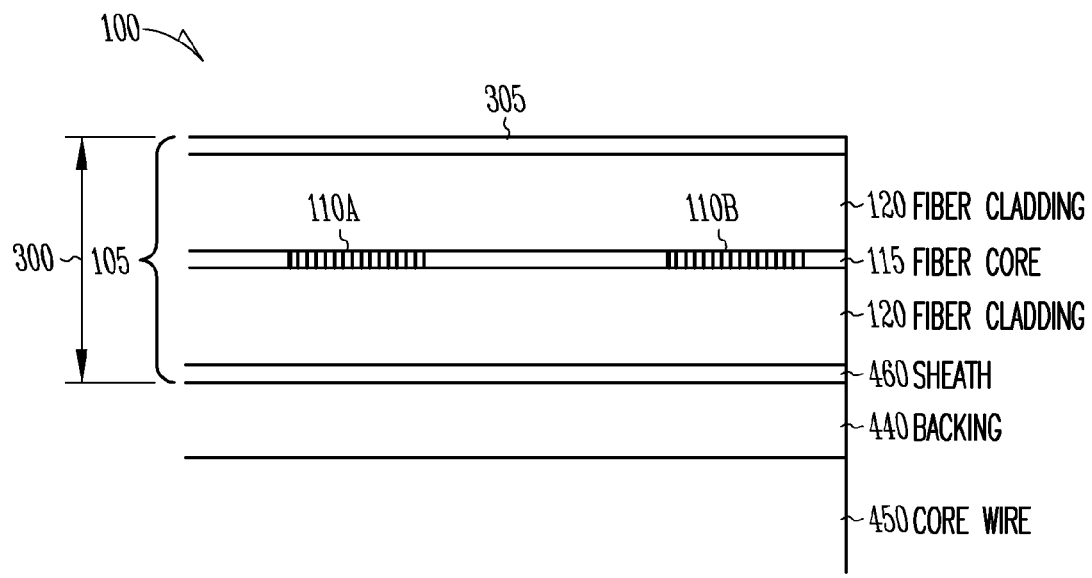
FIG. 4 is a cross-sectional schematic diagram illustrating generally another example of an FBG strain sensor in an optical fiber.

However, for a mechanically resonant transducer, reducing the thickness of fiber cladding 120, and therefore reducing the total size of the transducer, is limited by the wavelength of the acoustic energy to be received. In a fourth example, the thickness 300 of the strain sensing region is substantially less than half of the wavelength of the target acoustic energy. FIG. 4 is a cross-sectional schematic diagram illustrating such an example. In this example, the thickness 300 of the strain sensing region can be less than 60 micrometers. As the acoustic width of the transducer is reduced, the cross-sectional area of the transducer is reduced, and the total strain due to acoustic pressure on the transducer is reduced. Therefore, a smaller thickness 300 of the strain sensing region results in a smaller received acoustic signal, leading to reduced receive sensitivity of the FBG sensor 100. This reduced receive sensitivity of the FBG sensor 100 can be improved by placing a backing 440 between the strain sensing region of the optical fiber 105 and a core wire 450 that can be configured to provide support, rigidity, and flexibility for the assembly. The backing 440 can include a high acoustic impedance material such as a metal or ceramic. In an example, the backing 440 can be separated from the optical fiber such as by an acoustically thin (e.g., less than a quarter wavelength thick) tubular sheath 460. The coating 305 can also be configured, in an example, for acoustic impedance matching.

In an example, the backing 440 can be configured to reflect acoustic energy back to the strain sensing region, such as in a resonant manner, to increase the total amount of acoustic energy received by the strain sensing region and thereby increase the strain on the region. In this example, however, the receive sensitivity of FBG sensor 100 may depend on the polarization of the optical sensing signal because the backing 440 does not enhance the acoustic signal in all directions. The receive sensitivity generally is highest when the optical sensing signal is polarized parallel to an axis extending through the backing 440 and the fiber core 115 or an axis extending through the core wire 450 and the fiber core 115. The receive sensitivity is generally lowest when the angle of the polarization of the optical sensing signal is parallel to the outline of the interface between the backing 440 and the sheath 460, because the backing does not enhance the signal for this polarization orientation. The variable sensitivity in this example results at least partially from acoustic reflections from the backing 440 and from the core wire 450. The present applicant has recognized, among other things, that sensitivity to polarization of the optical sensing signal should be reduced or eliminated, if possible, in an example.

In an example, the backing 440 can be configured to absorb the acoustic energy that penetrates completely through the optical fiber to reach the backing 440. In this example, the backing 440 can be configured both to not reflect any acoustic energy back to FBG sensor 100 and also to inhibit or prevent the core wire 450 from reflecting any acoustic energy back to FBG sensor 100. The sheath 460 in this example can be configured to not reflect any substantial amount of acoustic energy. In an illustrative example, the sheath 460 can comprise a layer of UV-curable polyester such as with a thickness of about 10 micrometers or less. The backing 440 in this illustrative example can comprise microballoons filled with gas or microballoons filled with gas mixed into a polymer matrix. In an example of a device configured for imaging within a coronary vasculature, the room for the backing 440 is very limited, and therefore it can be advantageous if the backing 440 is relatively highly acoustically absorbent with a relatively small thickness. In an example in which acoustic energy that penetrates completely through the optical fiber to reach the backing 440 is substantially absorbed by a relatively small thickness of the backing 440, microballoons can comprise 30% to 50% of the volume of the backing 440. With such a polymer-microballoon mixture, the backing 440 can have a thickness of as little as 50 micrometers and can be configured to be capable of attenuating acoustic energy with a frequency of 20 megahertz by 17 decibels to 23 decibels per millimeter of thickness of the backing 440. In an example, the sensitivity of FBG sensor 100 is relatively independent of the polarization of the output optical beam within FBG sensor 100. In an example, a peak-to-peak amplitude of the oscillating output optical sensing signal varies by no more than one decibel as the polarization of the output optical sensing signal is rotated 90 degrees. In an example, the backing 440 attenuates ultrasound energy by at least 90%.

The above examples can be combined with each other or can include more or fewer elements than are recited in the examples and can still function as described in the examples. For example, an ultrasound-to-optical transducer that is relatively insensitive to the polarization of the optical sensing signal can include an optical fiber, a backing configured to absorb ultrasound energy that goes through the optical fiber to reach the backing, and an FBG interferometer configured to modulate an optical sensing signal in response to the ultrasound energy. The optical fiber can include a thickness of the optical fiber that is less than half the wavelength of the ultrasound energy that is sensed by the transducer.

3. Examples of Guidewire Design

Figure 5:
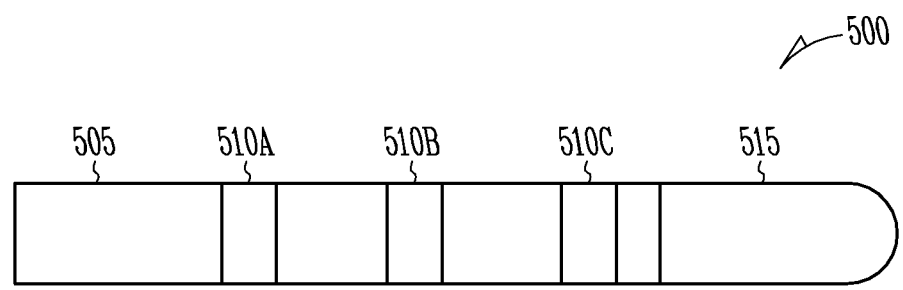
FIG. 5 is a schematic diagram that illustrates generally an example of a side view of a distal portion of a guidewire.

FIG. 5 is a schematic diagram that illustrates generally an example of a side view of a distal portion 500 of an imaging guidewire 505 or other elongated catheter (in an example, the guidewire 505 is sized and shaped and is of flexibility and rigidity such that it is capable of being used for introducing and/or guiding a catheter or other medical instrument, e.g., over the guidewire 505 within a living body). In this example, the distal portion 500 of the imaging guidewire 505 includes one or more imaging windows 510A, 510B, ..., 510N located slightly or considerably proximal to a distal tip 515 of the guidewire 505. Each imaging window 510 includes one or more acoustic-to-optical FBG sensors 100. In an example, the different imaging windows 510A, 510B, ..., 510N are designed for different optical wavelengths, such that particular individual windows can be addressed by changing the optical wavelength being communicated through fiber core 115.

Figure 6:
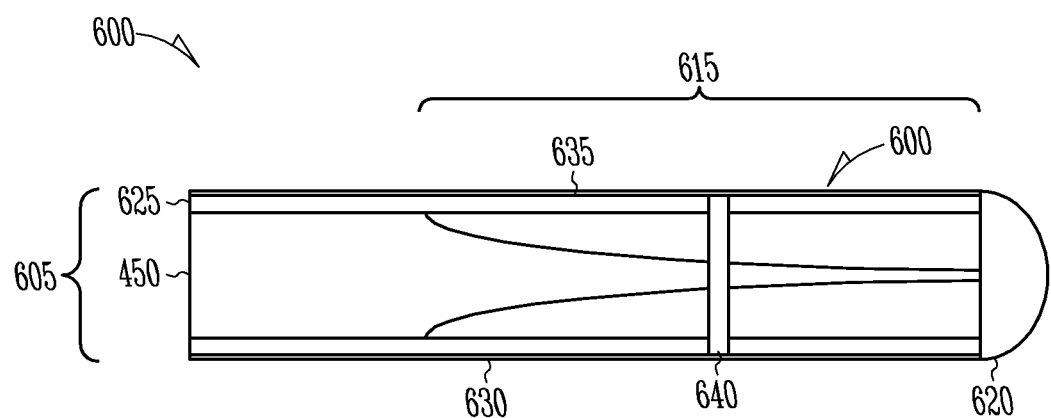
FIG. 6 is a schematic diagram that illustrates generally an example of a cross-sectional side view of a distal portion of a guidewire.

FIG. 6 is a schematic diagram that illustrates generally an example of a cross-sectional side view of a distal portion 600 of a guidewire 605. In this example, the guidewire 605 can include a solid metal or other core wire 450 that can taper down in diameter (e.g., from an outer diameter of about 0.011 inches) at a suitable distance 615 (e.g., about 50 cm) from the distal tip 620, to which the tapered-down distal end of core wire 450 can be attached. In this example, optical fibers 625 can be distributed around the outer circumference of the guidewire core 450, and can be attached to the distal tip 620. In this example, the optical fibers 625 can be at least partially embedded in a binder material (e.g., UV curable acrylate polymer) that bonds the optical fibers 625 to the guidewire core wire 450 or the distal tip 620. The binder material may also contribute to the torsion response of the resulting guidewire assembly 605. In an example, the optical fibers 625 and binder material can be overcoated with a polymer or other coating 630, such as for providing abrasion resistance, optical fiber protection, or friction control, or a combination thereof. At least one metallic or other bulkhead 640 can be provided along the tapered portion of the core wire 450. In an example, the optical fibers 625 and binder 635 can be attached to a proximal side of the bulkhead 640 such as near its circumferential perimeter. A distal side of the bulkhead 640 can be attached, such as near its circumferential perimeter, to a coil winding 610 that can extend further, in the distal direction, to a ball or other distal tip 620 of the guidewire 605. In this example, the composite structure of the distal region 600 of the guidewire 605 can provide, among other things, flexibility and rotational stiffness, such as for allowing the guidewire 605 to be maneuvered to an imaging region of interest such as within a vascular or any other lumen.

Figure 7:
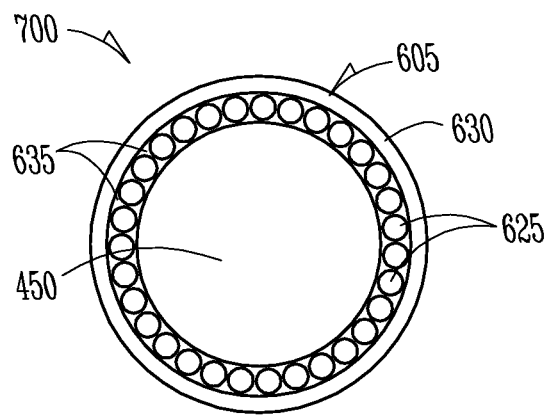
FIG. 7 is a schematic diagram that illustrates generally an example of a cross-sectional end view of a proximal portion of a guidewire.

FIG. 7 is a schematic diagram that illustrates generally an example of a cross-sectional end view of a proximal portion 700 of guidewire 605, which can include core wire 450, optical fibers 625, binder material 635, and outer coating 630. In this example, but not by way of limitation, the diameter of the core 450 can be about $11/1000$ inch, the diameter of the optical fibers 625 can be about $(1.25)/1000$ inch, and the optional outer coating 1030 can be about $(0.25)/1000$ inch thick.

Figure 8:
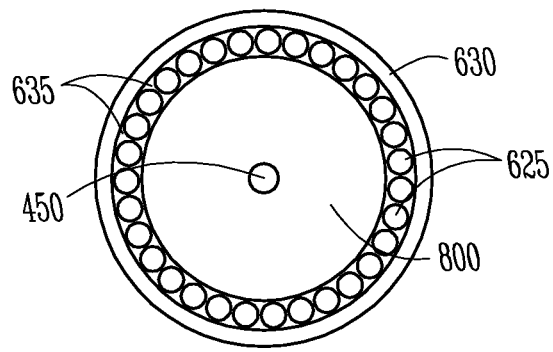
FIG. 8 is a schematic diagram that illustrates generally an example of a cross-sectional end view of a distal portion of a guidewire.

FIG. 8 is a schematic diagram that illustrates generally an example of a cross-sectional end view of the distal portion 600 of the guidewire 605, e.g., adjacent to the distal tip 620. In this example, but not by way of limitation, the diameter of core wire 450 has tapered down to about $1.5/1000$ inch, circumferentially surrounded by a void 800 of about the same outer diameter (e.g., about $11/1000$ inch) as the core wire 450 near the proximal end 700 of the guidewire 605. In this example, the optical fibers 625 can be circumferentially disposed in the binder material 635 around the void 800. Binder material 635 can provide structural support. Optical fibers 625 can be optionally overlaid with the outer coating 630.

4. Examples of Acoustic Transducer Construction

Figure 9:
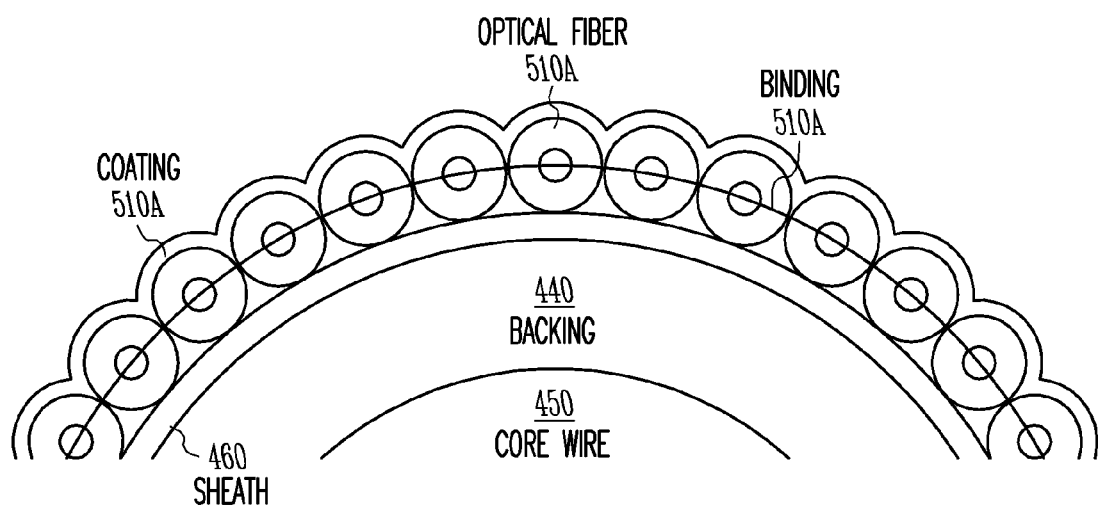
FIG. 9 is a cross-sectional end view that illustrates generally an example of a guidewire assembly at a location of a transducing window.

In an example, before one or more acoustic transducers are fabricated, the guidewire 605 can be assembled. FIG. 9 is a cross-sectional end view illustrating an example of a structure of such a guidewire assembly such as at a location of a transducing window 510. An example of such assembling can include placing the tubular sheath 460 on the core wire 450 such as at the locations selected for transducing, inserting the backing 440 into a gap between the core wire 450 and the tubular sheath 460, and binding the optical fibers 625 to the sheath 460 and the distal tip 620 or bulkhead 640. The coating 305, which, in an example, can include the outer coating 630, can then optionally be layered over the optical fibers 625. In another example of such assembling, the backing 440 can be formed to the surface of the core wire 450 such as at the locations selected for transducing, and the tubular sheath 460 can be formed to the exposed surface of the backing, such as by heat-shrinking, for example. In an example, the optical fibers 625 can each have a diameter of less than half of the wavelength of the acoustic energy that the acoustic transducers are designed to sense, although the diameter of each of the optical fibers 625 can be larger than this in other examples.

After the guidewire 605 has been assembled, the FBGs can be added to one or more portions of the optical fibers 625, such as within the transducer windows 510. In an example, an FBG can be created using an optical process in which a portion of the optical fiber 625 is exposed to a carefully controlled pattern of ultraviolet (UV) radiation that defines the Bragg grating. Then, a photoacoustic material or other desired overlayer can be deposited or otherwise added in the transducer windows 510 such as over the Bragg grating. Thus, in this example, the FBGs can be advantageously constructed after the optical fibers 625 have been mechanically assembled into the guidewire assembly 605.

An FBG writing laser can be used to expose the desired portion of the optical fiber 625 to a carefully controlled pattern of UV radiation to define the Bragg grating. The FBG writing laser can be operated so as to reduce the amount of birefringence caused by the FBGs. This will reduce the dependence of the FBG sensor 100 on the polarization of the optical sensing signal that is modulated by the received acoustic energy. In an illustrative example, at least one of hydrogen or deuterium can first be optionally infused into the optical fiber core 115. Conditions for diffusion of the gas into the fiber can be 150 atm pressure at room temperature for 1 to 10 days. Then, the optical fiber 625 can be exposed to the writing laser, such as for a time period of between about 30 seconds and about 10 minutes. In this example, the writing laser can have a pulse energy of between about 0.1 millijoules (mJ) and about 10 millijoules and can have a polarization angle that is substantially parallel to the longitudinal axis of the optical fiber core 115.

In an illustrative example, such as in which hydrogen is not infused into the optical fiber core 115, the optical fiber 625 can be exposed to the writing laser such as for a time period of between about 30 seconds and about 10 minutes. In this example, the writing laser can have a pulse energy of between about 0.1 millijoules and about 10 millijoules and a polarization angle that is substantially perpendicular to the longitudinal axis of the optical fiber core 115. In either this example or the above example in which hydrogen or deuterium is first optionally infused into the optical fiber core 115, desired portions of all layers or coverings over the fiber cladding 120 can optionally be removed before the optical fiber 625 is exposed to the writing laser.

In an example, the writing conditions can be controlled so that the FBG sensor 100 is relatively insensitive to the polarization of the output optical signal. This can include, for example, reducing the speed of writing by lowering the intensity of the UV lamp in order to reduce heating biases. In an example, the shift in the center wavelength of the skirt of the FBG sensor 100 as the polarization of the output optical sensing signal is rotated 90 degrees is less that half of the Full Width Half Maximum of the skirt of the FBG sensor 100. In another example, a total birefringence induced on an optical signal with a wavelength of about 1550 nanometers transmitted within the optical fiber 625 is less than $(3 \times 10^{-6})$.

Additional Notes

In this document, the term "minimally-invasive" refers to techniques that are less invasive than conventional surgery; the term "minimally-invasive" is not intended to be restricted to the least-invasive technique possible.

Although certain of the above examples have been described with respect to intravascular imaging (e.g., for viewing or identifying vulnerable plaque), the present systems, devices, and methods are also applicable to imaging any other body part. For example, the guidewire or other elongated body as discussed above can be inserted into a biopsy needle, laparoscopic device, or any other lumen or cavity such as for performing imaging. Moreover, such imaging need not involve insertion of an elongate body into a lumen, for example, an imaging apparatus can be wrapped around a portion of a region to be imaged.

In an example, the present systems, devices, and methods can be used to process the Doppler shift in acoustic frequency to image or measure blood flow. The operation can be similar to that described above, however, this would increase the length of the transmitted acoustic signal, and can use Doppler signal processing in the image processing portion of the control electronics. The transmitted acoustic signal can be lengthened, in an example, such as by repeatedly pulsing the transmit optical energy at the same rate as the desired acoustic frequency.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    an ultrasound-to-optical transducer, comprising:
        an optical fiber;
        a Fiber Bragg Grating (FBG) interferometer in the optical fiber, the FBG interferometer being configured for receiving ultrasound energy and for modulating an optical sensing signal, in response to the received ultrasound energy; and
        an ultrasound-absorptive backing that is more absorptive than the optical fiber.

2. The apparatus of claim 1, wherein the optical fiber includes an optical fiber diameter that is less than half of a wavelength of target ultrasound energy to be received by the transducer.

3. The apparatus of claim 2, wherein the optical fiber diameter is less than sixty micrometers.

4. The apparatus of claim 1, wherein the backing comprises microballoons containing a gas.

5. The apparatus of claim 4, wherein the microballoons comprise about 30% to about 50% of a volume of the backing.

6. The apparatus of claim 5, wherein a thickness of the backing is between about 25 micrometers and about 100 micrometers.

7. The apparatus of claim 1, wherein the transducer is configured such that a peak-to-peak amplitude of an oscillating output optical bias signal modulated by the transducer varies by no more than one decibel when the polarization angle of the optical sensing signal is varied by 90 degrees.

8. The apparatus of claim 1, wherein a total birefringence induced on an optical signal with a wavelength of about 1550 nanometers transmitted within the optical fiber is less than $(3 \times 10^{-6})$.

9. The apparatus of claim 1 comprising:
an elongated intravascular imaging assembly, comprising an external proximal portion comprising an optical signal interface and a distal portion sized and shaped and configured for internal intravascular acoustic imaging, the imaging assembly comprising:
an elongated support, extending substantially from the proximal portion of the imaging assembly to the distal portion of the imaging assembly, the support configured to provide adequate length, rigidity, and flexibility to permit intravascular introduction and steering of a distal portion of the imaging assembly to a location of interest;
the optical fiber, extending longitudinally and affixed along the support substantially from the proximal portion of the imaging assembly substantially to the distal portion of the imaging assembly;
a transducer, located at or near a distal portion of the imaging assembly and configured as at least one of the ultrasound-to-optical transducer or an optical-to-ultrasound transducer; and
the backing, located in a backing region between the transducer and the elongated support, the backing configured to attenuate ultrasound energy that passes through the optical fiber and reaches the backing region by at least 90%.

10. The apparatus of claim 9, wherein the assembly comprises:
a plurality of the optical fibers, extending longitudinally and affixed along the support, the fibers arranged circumferentially about a central longitudinal axis of the support; and
a plurality of the transducers, wherein at least one of the transducers includes a photoacoustic material located at a peripheral portion of at least one of the optical fibers that is away from the backing.

11. A method comprising:
fabricating an ultrasound-to-optical transducer, the fabricating comprising:
providing an optical fiber;
creating a Fiber Bragg Grating (FBG) interferometer in the optical fiber, the FBG interferometer being configured for receiving ultrasound energy and for modulating an optical sensing signal, in response to the received ultrasound energy; and
associating an ultrasound-absorptive backing with the optical fiber, wherein the backing is more absorptive than the optical fiber.

12. The method of claim 11, wherein providing an optical fiber comprises providing an optical fiber that includes an optical fiber diameter that is less than half of a wavelength of target ultrasound energy to be received by the transducer.

13. The method of claim 11, wherein associating the backing with the fiber comprises associating the backing comprising microballoons containing a gas with the fiber.

14. The method of claim 13, wherein associating the backing comprising microballoons with the fiber comprises providing the backing comprising the microballoons that comprise about 30% to about 50% of the volume of the backing.

15. The method of claim 14, wherein associating the backing comprising microballoons comprises inserting the backing into a backing region between a central support structure and the optical fiber, wherein both the support structure and the fiber extend longitudinally, the backing region being bounded laterally by a tubular sheath.

16. The method of claim 15, wherein providing the backing comprises conforming the backing to the external surface of a central support structure, wherein both the support structure and the fiber extend longitudinally.

17. The method of claim 16, wherein providing the backing further comprises conforming a tubular sheath to a surface of the backing that is away from the support structure.

18. An apparatus comprising:
an ultrasound-to-optical transducer, comprising:
an optical fiber;
a Fiber Bragg Grating (FBG) interferometer in the optical fiber, the FBG interferometer being configured for receiving ultrasound energy and for modulating an optical sensing signal, in response to the received ultrasound energy; and
an ultrasound-absorptive backing that is more absorptive than the optical fiber; and
a sheath positioned between the backing and the optical fiber, wherein the sheath and the backing are configured to absorb the ultrasound energy that pass through the optical fiber.

19. An apparatus comprising:
an ultrasound-to-optical transducer, comprising:
an optical fiber;
a Fiber Bragg Grating (FBG) interferometer in the optical fiber, the FBG interferometer being configured for receiving ultrasound energy and for modulating an optical sensing signal, in response to the received ultrasound energy; and
an ultrasound-absorptive backing configured for absorbing ultrasound energy that passes through and beyond the FBG interferometer in the optical fiber.

* * * * *